United States Patent
Suehara

(10) Patent No.: US 10,335,018 B2
(45) Date of Patent: Jul. 2, 2019

(54) ACTUATING MEMBER AND MEDICAL DEVICE

(71) Applicant: Terumo Kabushiki Kaisha, Tokyo (JP)

(72) Inventor: Satoru Suehara, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 590 days.

(21) Appl. No.: 14/871,241

(22) Filed: Sep. 30, 2015

(65) Prior Publication Data
US 2016/0015249 A1 Jan. 21, 2016

Related U.S. Application Data

(63) Continuation of application No. PCT/JP2013/059914, filed on Apr. 1, 2013.

(51) Int. Cl.
*A61B 1/005* (2006.01)
*A61B 17/34* (2006.01)
(Continued)

(52) U.S. Cl.
CPC .......... *A61B 1/0057* (2013.01); *A61B 1/0052* (2013.01); *A61B 17/3421* (2013.01);
(Continued)

(58) Field of Classification Search
CPC .......... A61M 25/0136; A61M 25/1038; A61M 25/0147; A61B 1/0057; A61B 1/0052;
(Continued)

(56) References Cited

U.S. PATENT DOCUMENTS 5,358,478 A * 10/1994 Thompson ........ A61M 25/0136
604/528
5,861,024 A * 1/1999 Rashidi .............. A61B 18/1492
600/374
(Continued)

FOREIGN PATENT DOCUMENTS

JP S63-035223 A 2/1988
JP H05-507212 A 10/1993
(Continued)

OTHER PUBLICATIONS

English-Language Translation of Notification of Reasons for Refusal issued in Japanese Patent Application No. 2015-509693 dated Dec. 20, 2016.
(Continued)

*Primary Examiner* — Kevin C Sirmons
*Assistant Examiner* — Leah J Swanson
(74) *Attorney, Agent, or Firm* — Foley & Lardner LLP

(57) ABSTRACT

An actuating member for making a flexible elongate member for medical use perform a predetermined action. The actuating member includes a push/pull member, an operating member, and a cam member. The push/pull member includes a first moving portion and a second moving portion, which are movable relative to each other. The push/pull member is pushed/pulled in conjunction with a movement of the first moving portion and the second moving portion. The operating member is rotatable about an axis in a direction intersecting an axial direction of the elongate member. The cam member moves the first moving portion and the second moving portion in conjunction with rotation of the operating member. The push/pull member makes the elongate member perform at least one of (i) an advance/retraction action and (ii) a bending action by transmitting the movement of the
(Continued)

first moving portion and the second moving portion to the elongate member.

11 Claims, 10 Drawing Sheets

(51) Int. Cl.
 *A61M 25/01* (2006.01)
 *A61B 17/00* (2006.01)
 *A61B 90/00* (2016.01)
(52) U.S. Cl.
 CPC .... *A61M 25/0138* (2013.01); *A61M 25/0147* (2013.01); *A61B 2017/00309* (2013.01); *A61B 2017/00327* (2013.01); *A61B 2090/3937* (2016.02); *A61M 25/0136* (2013.01)
(58) Field of Classification Search
 CPC .......... A61B 17/3421; A61B 2017/003; A61B 2017/00318; A61B 2017/00323; A61B 2017/00327
 USPC ...................................... 604/95.04
 See application file for complete search history.

(56) References Cited

U.S. PATENT DOCUMENTS

| | | |
|---|---|---|
| 2005/0107737 A1 | 5/2005 | McDaniel |
| 2008/0103520 A1* | 5/2008 | Selkee .............. A61M 25/0136 606/195 |
| 2008/0138886 A1 | 6/2008 | Murphy et al. |
| 2009/0084826 A1 | 4/2009 | Shah et al. |

FOREIGN PATENT DOCUMENTS

| | | |
|---|---|---|
| JP | 2005-144188 A | 6/2005 |
| JP | 2006-061176 A | 3/2006 |
| JP | 2008-142199 A | 6/2008 |
| JP | 2009-082704 A | 4/2009 |
| WO | WO-91/11213 A1 | 8/1991 |

OTHER PUBLICATIONS

International Search Report dated Apr. 23, 2013 issued in PCT/JP2013/059914.

* cited by examiner

ACTUATING MEMBER AND MEDICAL DEVICE

CROSS-REFERENCE TO RELATED PATENT APPLICATION

This application is a continuation application of and claims the benefit of priority from International Patent Application No. PCT/JP2013/059914, filed Apr. 1, 2013, the contents of which are incorporated herein by reference.

BACKGROUND

The present disclosure relates to an actuating member for making a medical elongate member perform a predetermined action, and a medical device equipped with the actuating member.

In the medical field, a flexible elongate member is generally used as a medical device for performing administration of medicine into a living body, suction or injection of various fluids, introduction of other medical devices into the living body, or the like. For example, where an elongate member is used for the introduction of other medical devices, prior to the introduction of the medical device, the elongate member is inserted into a lumen (a blood vessel, a body cavity, or the like) of the living body, and is guided to a target area, such as an area to be treated and its peripheral area. In order to appropriately guide the elongate member to the target area during such use, it is often necessary to introduce the elongate member along a curved path like the lumen of the living body. For this reason, the elongate member may include an actuating member capable of performing an arbitrary bending operation by a user's proximal operation when the elongate member is used.

As to techniques related to this, Japanese Patent Laid-Open No. 2008-142199 (hereinafter referred to as "Patent Document 1") describes an actuating member, which includes a push/pull member connected to an elongate member, a pulley around which the push/pull member is wound and a handle for rotationally actuating the pulley, and an endoscope into which the actuating member is assembled. In this actuating member, the handle is arranged on a proximal side of the endoscope and rotates around an axis orthogonal to the axial direction of the elongate member, thereby winding the push/pull member to perform a bending operation.

SUMMARY

In the actuating member of Patent Document 1, the push/pull member is arranged so as to be wound around the pulley and an action direction in which the push/pull member is pushed/pulled is converted from a straight direction into a circumferential direction for bending. Therefore, a wire with relatively small rigidity or the like is used as the push/pull member. For this reason, there is a possibility that a push/pull force will not be reliably transmitted to the elongate member via this wire.

Additionally, because it is necessary to wind the wire around the pulley with good trackability, the pulley must be large, causing the entire device to be large.

Disclosed herein is an actuating member by which an advance/retraction movement of a push/pull member can be efficiently transmitted to an elongate member and which enables a smaller medical device to be realized, and a medical device equipped with the actuating member.

The object of certain embodiments of the present disclosure will be achieved by any one of the followings.

In one aspect, an actuating member for making a flexible elongate member for medical use perform a predetermined action includes a push/pull member, an operating member, and a cam member. The push/pull member includes a first moving portion and a second moving portion which are disposed on a proximal side regarding an axial direction of the elongate member and which are movable relative to each other in the axial direction of the elongate member. The push/pull member further includes a first extending portion that extends from the first moving portion toward a distal side regarding the axial direction of the elongate member and a second extending portion that extends from the second moving portion toward the distal side regarding the axial direction of the elongate member. The push/pull member is pushed/pulled in the axial direction of the elongate member in conjunction with a movement of the first moving portion and the second moving portion. The operating member effects the movement of the first moving portion and the second moving portion and is provided to be rotatable about an axis in a direction intersecting the axial direction of the elongate member. The cam member is configured to make contact with the first moving portion and the second moving portion and to move the first moving portion and the second moving portion in conjunction with rotation of the operating member. The push/pull member is capable of making the elongate member perform at least one of (i) an advance/retraction action and (ii) a bending action, by transmitting the movement of the first moving portion and the second moving portion, which are moved by the cam member, to the elongate member.

According to the actuating member configured as above, the push/pull member is pushed/pulled in the axial direction of the elongate member, without conversion of its action direction, and the elongate member is thereby made to perform an advance/retraction action or a bending action. Therefore, the advance/retraction movement of the push/pull member can be efficiently transmitted to the elongate member. In addition, because it is unnecessary to wind the push/pull member around the operating member, a medical device reduced in overall size can be realized.

In the actuating member as above, the cam member may be configured to move the first moving portion and the second moving portion in opposite directions along the axial direction, and the movement of the first moving portion and the second moving portion makes the elongate member perform the bending action.

According to this configuration, a bending action of the elongate member is effected by moving the first moving portion and the second moving portion in the opposite directions. Therefore, the elongate member can be bent with reduced traveling distances of the first moving portion and the second moving portion. Consequently, operability of the actuating member is enhanced.

In the actuating member as above, the cam member may be configured to move the first moving portion and the second moving portion with different traveling distances, in the same direction along the axial direction, and the movement of the first moving portion and the second moving portion makes the elongate member perform both (i) the advance/retraction action and (ii) the bending action.

According to this configuration, a bending action of the elongate member is effected by moving the first moving portion and the second moving portion in the same direction. Therefore, the elongate member can be made to perform a bending action while performing an advance/retraction action. Consequently, an actuating member with enhanced performance can be provided.

In the actuating member as above, the cam member may be composed of a single member having a first cam surface that makes contact with the first moving portion and a second cam surface that makes contact with the second moving portion.

According to this configuration, because the cam member is composed of the single member, the elongate member can be bent with a simple configuration. Therefore, a medical device can be more reduced in overall size.

In the actuating member as above, the cam member may be formed to be integral with the operating member.

According to this configuration, because the cam member is formed integral with the operating member, it is unnecessary to provide a transmission mechanism for transmitting a rotating force of the operating member to the cam member. Therefore, a further reduction in the overall size of the medical device can be realized.

In the actuating member as above, the cam member may be composed of a first cam member and a second cam member provided separately from the first cam member. The first cam member may have a first cam surface that makes contact with the first moving portion, the second cam member may have a second cam surface that makes contact with the second moving portion.

According to this configuration, the first cam member and the second cam member, which are separate bodies from each other, constitute the cam member. Therefore, the first cam member and the second cam member can be made to rotate in different amounts per one revolution of the operating member and/or in the rotating direction. Consequently, movements of the first moving portion and the second moving portion attendant on rotation of the operating member can be precisely set, whereby the degree of freedom in setting the bending of the elongate member can be enhanced.

In the actuating member having a first cam member and a second cam member as above, one of the first cam member and the second cam member may be formed to be integral with the operating member.

According to this configuration, since one of the first cam member and the second cam member is formed integral with the operating member, it is unnecessary to provide a transmission mechanism for transmitting a rotating force of the operating member to the cam member. Therefore, a medical device with a further reduced overall size can be realized.

The actuating member as above may further include a visual recognition portion which enables at least a bending amount, of an advance/retraction amount and the bending amount of the elongate member, to be confirmed by visual recognition.

According to this configuration, since at least one of the advance/retraction amount and the bending amount of the elongate member can be confirmed by the visual recognition portion, operability of the actuating member is enhanced.

In another aspect, a medical device includes: the actuating member as above, and a flexible elongate member which is made by the actuating member to perform at least one of (i) an advance/retraction action and (ii) a bending action.

According to this aspect, it is possible to provide a medical device equipped with an actuating member by which an advance/retraction movement of a push/pull member can be efficiently transmitted to an elongate member and a medical device with a reduced overall size can be realized.

DETAILED DESCRIPTION OF THE EMBODIMENTS

Figure 1:
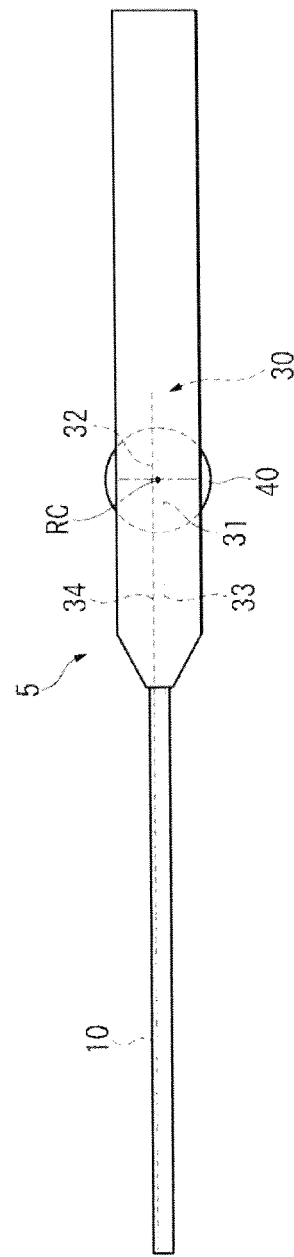
FIG. 1 is a schematic view of a medical device according to a first embodiment of the present disclosure.

Preferred embodiments of the present disclosure will be described below, referring to the drawings. Note that dimensional relations in the drawings may be exaggerated for convenience of explanation and may therefore be different from the actual ratios. In the following description, the operator's proximal side of a medical device according to each embodiment of the present disclosure will be referred to as the "proximal side," and the side of insertion into a living body lumen will be referred to as the "distal side."

First Embodiment

A configuration of a medical device 1 according to a first embodiment of the present disclosure will be described.

Figure 2:
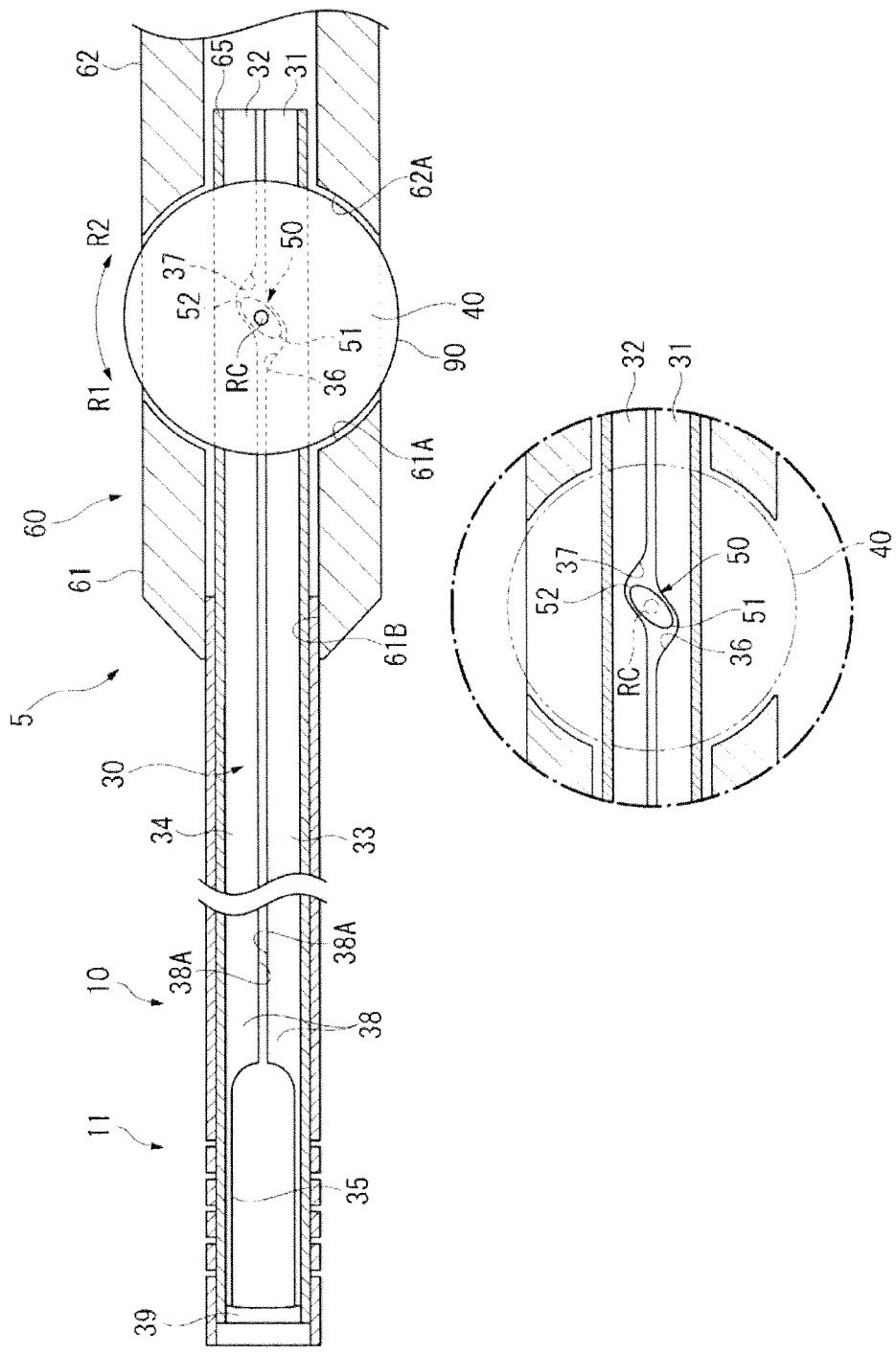
FIG. 2 is a side sectional view of the medical device according to the first embodiment.

FIG. 1 is a schematic view of the medical device 1 according to the first embodiment of the present disclosure. FIG. 2 is a side sectional view of the medical device 1 according to the first embodiment.

The medical device 1 according to the first embodiment of the present disclosure, as shown in FIG. 1, includes a flexible elongate member 10 for medical use, and an actuating member 5 for making the elongate member 10 perform a predetermined action. The actuating member 5 has a push/pull member 30, which includes a plurality of divided portions 38 to be described later. The push/pull member 30 further includes a first moving portion 31 and a second moving portion 32 that are disposed on a proximal side in an axial direction of the elongate member 10 and are movable relative to each other in the axial direction of the elongate member 10. A first extending portion 33 extends from the first moving portion 31 toward a distal side in the axial direction of the elongate member 10, and a second extending portion 34 extends from the second moving portion 32 toward the distal side in the axial direction of the elongate member 10. The push/pull member 30 is pushed/pulled in the axial direction of the elongate member 10 in conjunction with movement of the first moving portion 31 and the second moving portion 32. The actuating member 5 further includes an operating member 40 and a cam member 50. The operating member 40 effects movement of the first moving portion 31 and the second moving portion 32 and is capable of rotating about an axis in a direction intersecting the axial direction of the elongate member 10 at a rotation center RC. The cam member 50 is configured to make contact with the first moving portion 31 and the second moving portion 32 and to move the first moving portion 31 and the second moving portion 32 in conjunction with rotation of the operating member 40. The push/pull member 30 is capable of making the elongate member 10 perform a bending action by transmitting the movement of the first moving portion 31 and the second moving portion 32, which are moved by the cam member 50, to the elongate member 10.

As shown in FIG. 2, the actuating member 5 includes the push/pull member 30, which is pushed/pulled in the axial direction of the elongate member 10 in conjunction with movement of the first moving portion 31 and the second moving portion 32, and the operating member 40 for effecting movement of the first moving portion 31 and the second moving portion 32, and which is capable of rotating about the axis intersecting the axial direction of the elongate member 10 at the rotation center RC. The actuating member 5 also includes the cam member 50, which includes a first cam surface 51 that contacts the first moving portion 31 and a second cum surface 52 that contacts the second moving portion 32, and is configured to move the first moving portion 31 and the second moving portion 32 in conjunction with rotation of the operating member 40. The actuating member 5 further includes a sealing portion 65, which is provided at an outer periphery of the push/pull member 30 and which seals a fluid flowing through the inside of the push/pull member 30, a base portion 60, which is provided at an outer periphery on the proximal side of the sealing portion 65 and which supports the elongate member 10, the push/pull member 30, and the operating member 40, and a visual recognition portion 90, which enables a bending amount (bending angle) of the elongate member 10 to be confirmed by visual recognition.

Figure 3:
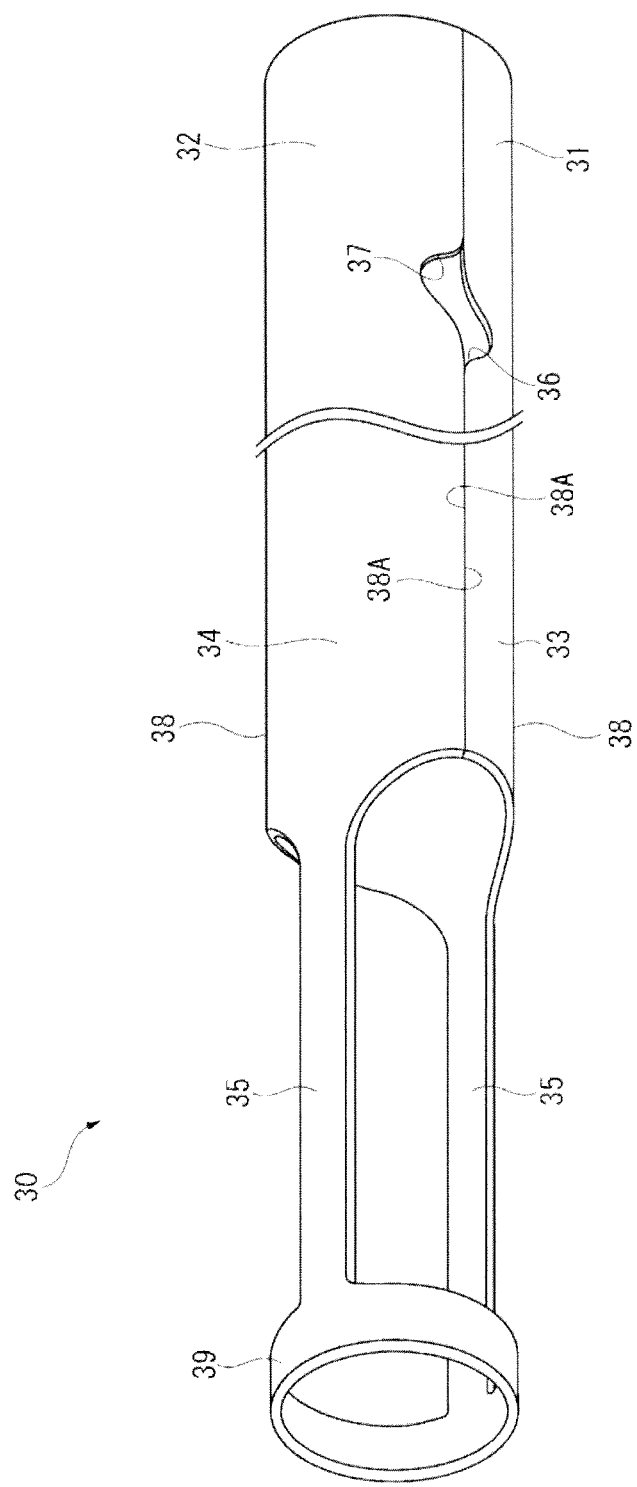
FIG. 3 is a perspective view of a push/pull member.

FIG. 3 is a perspective view of the push/pull member 30.

As shown in FIG. 3, the push/pull member 30 includes the plurality of divided portions 38, which are divided in the circumferential direction and together form a tube-shaped structure, and an annular connecting portion 39, which connects the tips regarding the axial direction of the divided portions 38. In conjunction with movement of the first moving portion 31 and the second moving portion 32, the divided portions 38 are pushed/pulled in the axial direction of the elongate member 10, thereby making the elongate member 10 perform a bending action.

The divided portions 38 include the first moving portion 31 and the second moving portion 32, which are disposed on the proximal side in the axial direction of the elongate member 10 and which are provided to be movable along the axial direction of the elongate member relative to each other. The divided portions 38 also include first extending portion 33, which extends from the first moving portion 31 toward the distal side of the elongate member 10 in the axial direction, the second extending portion 34, which extends from the second moving portion 32 toward the distal side of the elongate member 10 in the axial direction, and bending portions 35, which are provided on the distal side of the first extending portion 33 and the second extending portion 34 and which are bent by the pushing/pulling of the first extending portion 33 and the second extending portion 34 relative to each other. Note that it is sufficient for the push/pull member 30 to be capable of pushing/pulling the distal side of the elongate member 10, and, therefore, the push/pull member 30 may be, for example, a traction wire, a plate-shaped belt member or the like.

The first moving portion 31 has a first locking portion 36 on which the first cam surface 51 side of the cam member 50 is locked. The first locking portion 36 is provided on the distal side of the rotation center RC of the operating member 40 when the bending portions 35 are not bent, and has a shape such that a divided surface 38A is cut out. The first locking portion 36 is formed in a roughly triangular shape that opens wider toward the second moving portion 32.

The second moving portion 32 has a second locking portion 37 on which the second cam surface 52 side of the cam member 50 is locked. The second locking portion 37 is provided on the proximal side of the rotation center RC of the operating member 40 (on the proximal side compared to the first locking portion 36) when the bending portions 35 are not bent, and has a shape such that the divided surface 38A is cut out. The second locking portion 37 is formed in a roughly triangular shape that opens wider toward the first moving portion 31.

The first extending portion 33 transmits movement of the first moving portion 31 to the bending portion 35.

The second extending portion 34 transmits movement of the second moving portion 32 to the bending portion 35.

The bending portions 35 are each obtained by cutting out a portion of circumferential end edges of the divided portions 38 on the distal side and are each formed to be narrower than the first extending portion 33 and the second extending portion 34.

Since the push/pull member 30 is configured as above, it is ensured that when the first extending portion 33 is located on the distal side as compared to the second extending portion 34 due to the movement of the first moving portion 31 and the movement of the second moving portion 32, the bending portions 35 are bent upward, and when the first extending portion 33 is located on the proximal side as compared to the second extending portion 34, the bending portions 35 are bent downward.

The operating member 40, as shown in FIG. 2, is configured to be capable of moving each of the first moving portion 31 and the second moving portion 32 in opposite directions along the axial direction, and the movement of the first moving portion 31 and the second moving portion 32 makes the elongate member 10 perform a bending action. In addition, the operating member 40 is composed of a disk-shaped member whose disk surface is formed with the cam member 50 such that an operation to effect the movement of the first moving portion 31 and the second moving portion 32 can be accomplished by rotating the operating member 40. In conjunction with the rotation of the operating member 40, the first moving portion 31 and the second moving portion 32 are relatively moved closer to or away from each other, thereby bending the elongate member 10. Further, the operating member 40 has an outer peripheral surface that is rugged (projections and recesses) (not shown), which enables the operating member 40 to be rotated by an operator's fingers.

The cam member 50 is composed of a single member having the first cam surface 51 and the second cam surface 52. The cam member 50 extends from the rotation center RC of the operating member 40 toward one side and the other side with respect to a radial direction of the operating member 40 and is formed to be integral with the operating member 40.

The first cam surface 51 is provided on one end side of the cam member 50.

The second cam surface 52 is provided on the other end side of the cam member 50.

Here, the first cam surface 51 side of the cam member 50 is locked on the first locking portion 36, while the second cam surface 52 side of the cam member 50 is locked on the second locking portion 37. For this reason, as the operating member 40 rotates, the first cam surface 51 guides the first locking portion 36 in the axial direction of the elongate member 10 while making sliding contact with the first locking portion 36, whereas the second cam surface 52 guides the second locking portion 37 in the axial direction of the elongate member 10 while making sliding contact with the second locking portion 37. Specifically, when the operating member 40 is rotated in a direction R1, the cam member 50 moves the first moving portion 31 toward the proximal side and moves the second moving portion 32 toward the distal side. When the operating member 40 is rotated in a direction R2, the cam member 50 moves the first moving portion 31 toward the distal side and moves the second moving portion 32 toward the proximal side.

The sealing portion 65 seals a fluid flowing through the inside of the push/pull member 30. The sealing portion 65 is fixed in close contact with an outer periphery of the push/pull member 30. The fixing method is not particularly limited. For example, fixation may be accomplished by an adhesive, brazing, fusing, or the like. Examples of a material constituting the sealing portion 65 include thermoplastic resins that are excellent in biocompatibility, such as fluororesins, such as ETFE (ethylene-tetrafluoroethylene copolymer), PTFE (polytetrafluoroethylene), etc., polyolefins, such as PE (polyethylene), PP (polypropylene), etc., polyamides, polyesters, and polyurethane. Note that the sealing portion 65 may be disposed inside the push/pull member 30.

The base portion 60 supports the elongate member 10, the push/pull member 30, and the operating member 40. The base portion 60 includes a supporting portion 61, which is disposed on the distal side as compared with the operating member 40 and which supports the elongate member 10, the push/pull member 30, and the operating member 40, and a gripping portion 62, which is disposed on the proximal side relative to the operating member 40, supports the push/pull member 30 and the operating member 40, and is gripped when an operator performs a procedure. The base portion 60 is formed, for example, of a rigid resin material.

The supporting portion 61 supports the elongate member 10, the push/pull member 30, and the operating member 40. The supporting portion 61 includes a recessed portion 61A provided on the proximal side for accommodating the operating member 40 and an opening portion 61B, which is provided on the distal side and in which the elongate member 10 is inserted.

The gripping portion 62 supports the push/pull member 30 and the operating member 40, and is gripped when an operator performs a procedure. The gripping portion 62 has a recessed portion 62A provided on the distal side for accommodating the operating member 40.

The visual recognition portion 90 is provided on a disk surface or an outer peripheral surface of the operating member 40, and enables a bending amount of the elongate member 10 bent in conjunction with movement of the first moving portion 31 and the second moving portion 32 to be confirmed by visual recognition. The visual recognition portion 90 may be, for example, a marker; however, it is not limited to a marker, and may be a scale or the like.

The elongate member 10 is inserted in the opening portion 61B on the proximal side thereof and is bent on the distal side thereof through bending of the bending portions 35. The elongate member 10 includes on the distal side thereof rigidity-weakened portions 11, which can be easily bent. In this embodiment, the rigidity weakened portions 11 are each configured as a combination of tube-shaped members of a metal, such as stainless steel, which is ordinarily used for an endoscope or the like. The rigidity weakened portions 11 are provided at two positions (an upper position and a lower position), but it is sufficient that the rigidity weakened portions are provided on at least one side. Examples of a material usable for the elongate member 10 include thermoplastic resins that are excellent in biocompatibility, such as fluororesins, such as ETFE (ethylene-tetrafluoroethylene copolymer), PTFE (polytetrafluoroethylene), etc., polyolefins, such as PE (polyethylene), PP (polypropylene), etc., polyamides, polyesters, and polyurethane. In this case, the rigidity weakened portions 11 may be, but are not restricted to, slits. The rigidity weakened portions 11 may be configured using a material lower in rigidity than other portions.

Figure 4:
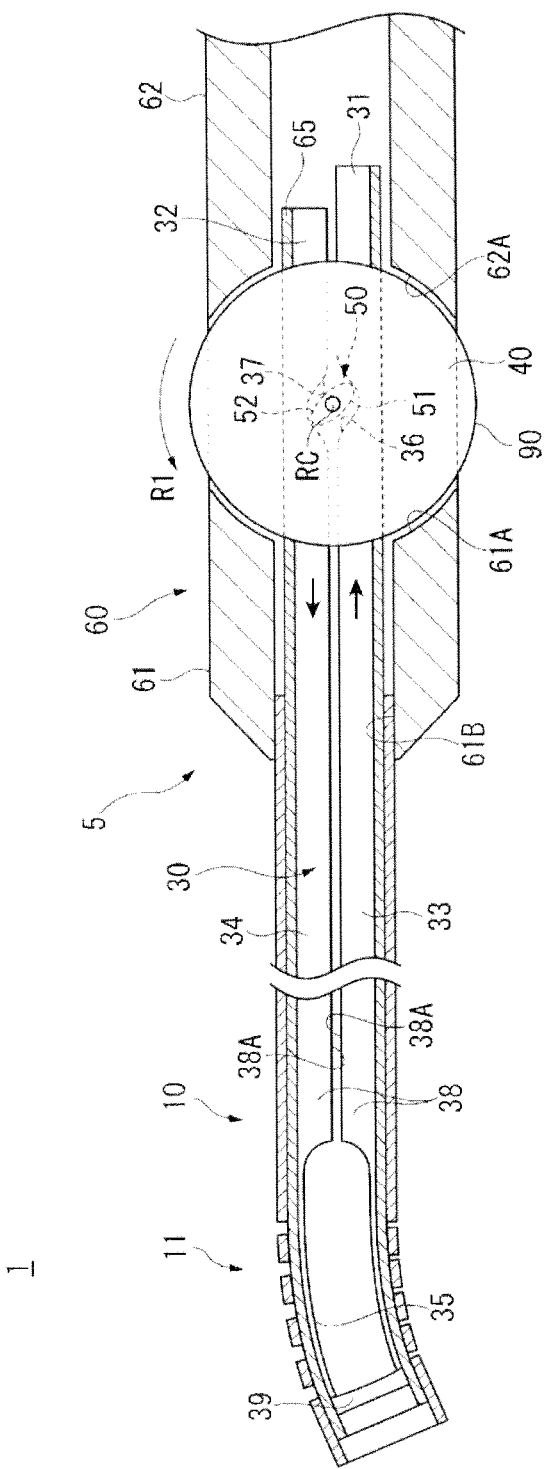
FIG. 4 is a side sectional view showing the medical device when a distal side of an elongate member is bent downward in the first embodiment.

A method of bending the elongate member 10 by the actuating member 5 according to the first embodiment of the present disclosure will be described below, referring to FIG. 4. FIG. 4 is a side sectional view showing the medical device 1 when the distal side of the elongate member 10 is bent downward.

When an operator, as shown in FIG. 4, rotates the operating member 40 in the direction R1, the first moving portion 31 is moved toward the proximal side as the first locking portion 36 is guided by the first cam surface 51, while the second moving portion 32 is moved toward the distal side as the second locking portion 37 is guided by the second cam surface 52. Consequently, the first extending portion 33 is moved toward the proximal side, while the second extending portion 34 is moved toward the distal side. When the first extending portion 33 is moved toward the proximal side and the second extending portion 34 is moved toward the distal side, the bending portions 35 are bent downward. With the bending portions 35 thus bent downward, the distal side of the elongate member 10 is bent downward.

Thus, according to the first embodiment of the present disclosure, the push/pull member 30 is pushed/pulled in the axial direction of the elongate member 10, without conversion of its action direction, thereby making the elongate member 10 perform a bending action. Therefore, the advance/retraction movement of the push/pull member 30 can be efficiently transmitted to the elongate member 10. Because it is unnecessary to wind the push/pull member 30 around the operating member 40, the medical device 1 can be made smaller in overall size.

In addition, the operating member 40 is so configured that the first moving portion 31 and the second moving portion 32 can be moved in opposite directions along the axial direction, and movement of the first moving portion 31 and the second moving portion 32 makes the elongate member 10 perform a bending action. Accordingly, the elongate member 10 can be bent with smaller traveling distances of the first moving portion 31 and the second moving portion 32, and operability of the actuating member 5 is enhanced.

Moreover, because the cam member 50 is composed of a single member, the elongate member 10 can be bent with a simple configuration, so that the medical device 1 can be made smaller in overall size.

Further, because the cam member 50 is formed to be integral with the operating member 40, it is unnecessary to provide a transmission mechanism for transmitting a rotating force of the operating member 40 to the cam member 50, allowing the medical device 1 to be made even smaller in overall size.

In addition, the actuator member 5 further includes the visual recognition portion 90, which enables the bending amount of the elongate member 10 to be confirmed by visual recognition. Therefore, the bending amount of the elongate member 10 can be confirmed through the visual recognition portion 90, which enhances operability of the actuating member 5.

In addition, it is possible to provide a medical device 1 equipped with the actuating member 5 by which the advance/retraction movement of the push/pull member 30 can be efficiently transmitted to the elongate member 10 and the medical device 1 can be made smaller in overall size.

Second Embodiment

A second embodiment of the present disclosure will be described below. Descriptions of features common to the first and second embodiments will be omitted, and features characteristic of only the second embodiment will be described.

Figure 5:
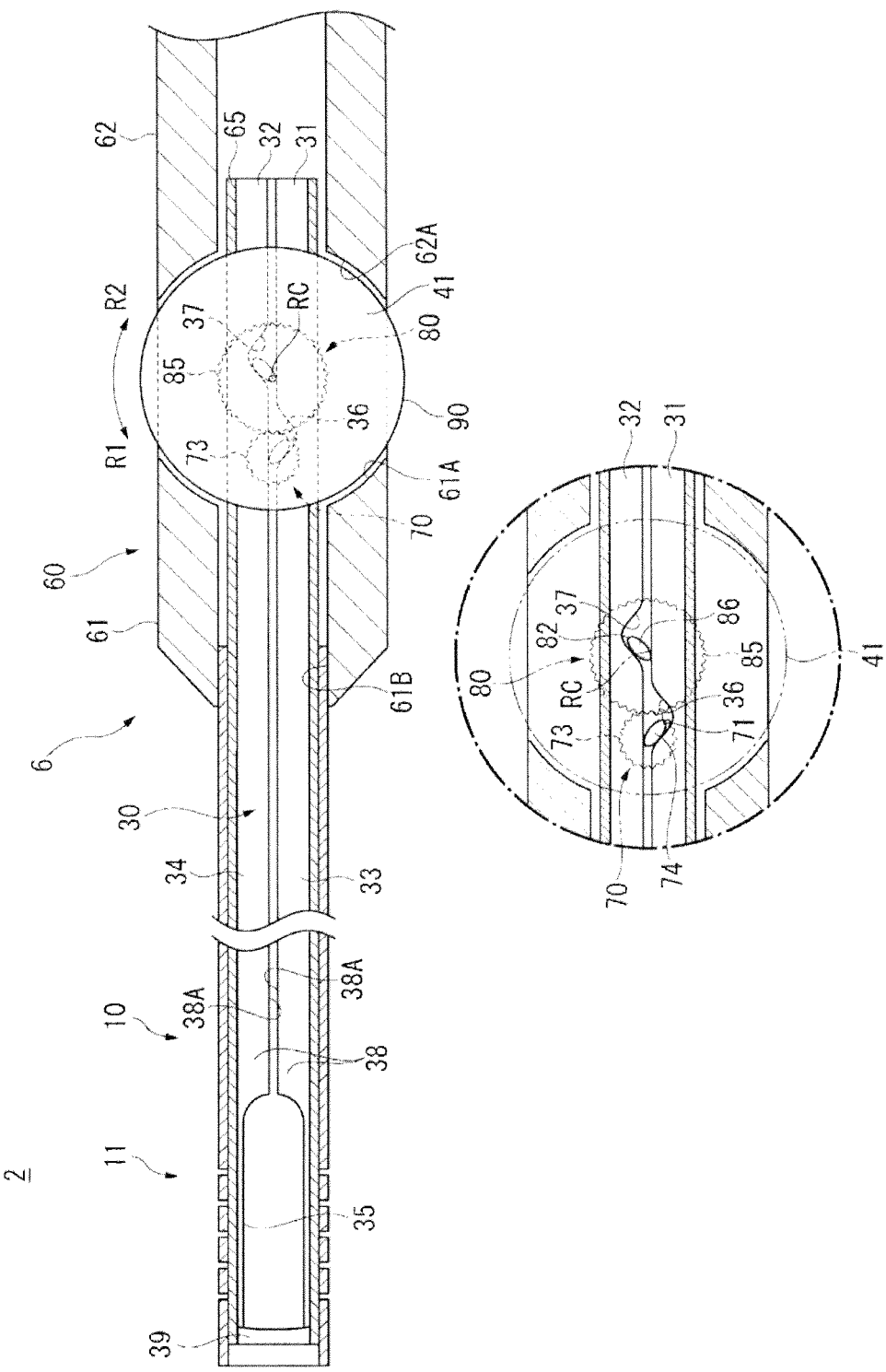
FIG. 5 is a side sectional view of a medical device according to a second embodiment of the present disclosure.

FIG. 5 is a side sectional view of a medical device 2 according to the second embodiment of the present disclosure.

The medical device 2 according to the second embodiment of the present disclosure, as shown in FIG. 5, includes an actuating member 6, which includes an operating member 41 for effecting a movement of a first moving portion 31 and a second moving portion 32 and being capable of rotating about an axis in a direction intersecting the axial direction of the elongate member 10 at a rotation center RC, a first cam member 70, that has a first cam surface 71 that makes contact with the first moving portion 31 and that functions as a cam member for moving the first moving portion 31 in conjunction with rotation of the operating member 41, and a second cam member 80 that has a second cam surface 82 that makes contact with the second moving portion 32 and that functions as a cam member for moving the second moving portion 32. The actuating member 6 further includes a visual recognition portion 90 which enables an advance/retraction amount and a bending amount (bending angle) of the elongate member 10 to be confirmed by visual recognition. The other features of the actuating member 6 are the same as in the first embodiment.

The operating member 41 is configured to be capable of moving the first moving portion 31 and the second moving portion 32 with different traveling distances in the same direction along the axial direction. The movement of the first moving portion 31 and the second moving portion 32 makes the elongate member 10 perform an advance/retraction action and a bending action. In addition, the operating member 41 is composed of a disk-shaped member having a disk surface formed with the second cam member 80 for meshing with the first cam member 70, and is so provided such that movement of the first moving portion 31 and the second moving portion 32 can be accomplished by rotating the operating member 41. As the operating member 41 rotates, the operating member 41 causes the first moving portion 31 and the second moving portion 32 to relatively move away from each other, thereby bending the elongate member 10.

The first cam member 70 includes a first gear portion 73 formed with teeth at a peripheral surface thereof, and a first cam portion 74 provided on a surface on one side of the first gear portion 73.

The first gear portion 73 is capable of rotating in conjunction with, and in a direction opposite to, the rotation of the operating member 41.

The first cam portion 74 extends from the rotation center of the first gear portion 73 toward one side along a radial direction of the first gear portion 73, and is provided with the first cam surface 71 at a tip portion thereof. The first cam portion 74 is locked on a first locking portion 36 on the first cam surface 71 side thereof, and, in conjunction with rotation of the operating member 41, the first cam surface 71 guides the first locking portion 36 in the axial direction of the elongate member 10 while making sliding contact with the first locking portion 36. Specifically, the first cam portion 74 is so formed that when the operating member 41 rotates in a direction R1, the first cam portion 74 moves the first moving portion 31 toward the distal side. When the operating member 41 rotates in a direction R2, the first cam portion 74 moves the first moving portion 31 toward the proximal side of the elongate member 10.

The second cam member 80 includes a second gear portion 85 that is provided on a surface on one side of the operating member 41 and that meshes with the first gear portion 73, and a second cam portion 86 provided on an opposite surface of the operating member 41 at the second gear portion 85. The second cam member 80 is formed to be integral with the operating member 41.

The second gear portion 85 is provided on the disk surface of the operating member 41, coaxially with the operating member 41, and has a rotation center coinciding with the rotation center RC of the operating member 41. The second gear portion 85 is formed to be greater than the first gear portion 73 and includes a larger number of teeth compared to the first gear portion 73.

The second cam portion 86 extends from the rotation center of the second gear portion 85 toward one side along a radial direction of the second gear portion 85 and is provided with the second cam surface 82 at a tip portion thereof. The second cam portion 86 is locked on a second locking portion 37 on the second cam surface 82 side thereof and, in conjunction with rotation of the operating member 41, the second cam surface 82 guides the second locking portion 37 in the axial direction of the elongate member 10 while making sliding contact with the second locking portion 37. Specifically, the second cam portion 86 is so formed that when the operating member 41 rotates in the direction R1, the second cam portion 86 moves the second moving portion 32 toward the distal side and, when the operating member 41 rotates in the direction R2, the second cam portion 86 moves the second moving portion 32 toward the proximal side of the elongate member 10.

Figure 6:
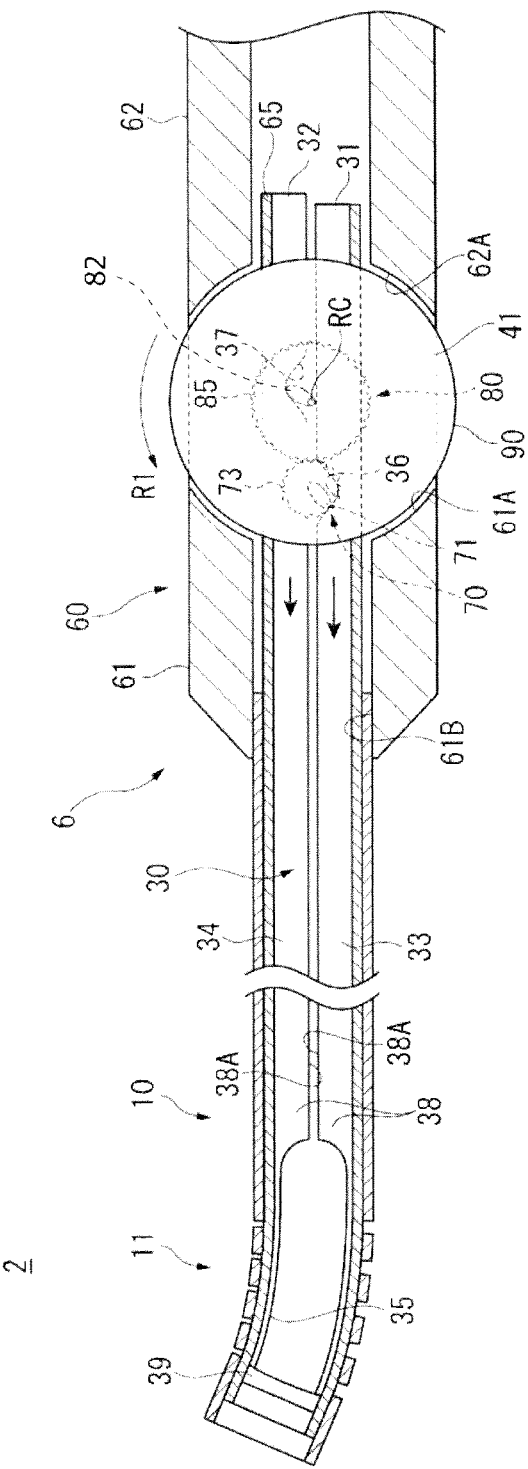
FIG. 6 is a side sectional view showing the medical device when a distal side of an elongate member is bent upward in the second embodiment.

A method of bending the distal side of the elongate member 10 by the actuating member 6 according to the second embodiment of the present disclosure will be described below, referring to FIG. 6. FIG. 6 is a side sectional view showing the medical device 2 when the distal side of the elongate member 10 is bent upward.

An operator, as shown in FIG. 6, rotates the operating member 41 in the direction R1. As a result, the first moving portion 31 is moved toward the distal side as the first locking portion 36 is guided by the first cam surface 71 and the second moving portion 32 is also moved toward the distal side as the second locking portion 37 is guided by the second cam surface 82. In this instance, because the second gear portion 85 has a larger number of teeth compared to the first gear portion 73, a rotation amount of the first gear portion 73 will be greater than a rotation amount of the second gear portion 85 such that the first moving portion 31 is moved more toward the distal side than the second moving portion 32. Therefore, the bending portions 35 are bent upward while being moved toward the distal side. When the bending portions 35 are bent upward while being moved toward the distal side, the distal side of the elongate member 10 is bent upward and is moved toward the distal side.

Thus, according to the second embodiment of the present disclosure, the push/pull member 30 is pushed/pulled in the axial direction of the elongate member 10, without conversion of its action direction, to thereby make the elongate member 10 perform an advance/retraction action and a bending action. Therefore, the advance/retraction movement of the push/pull member 30 can be efficiently transmitted to the elongate member 10. In addition, because it is unnecessary to wind the push/pull member 30 around the operating member 41, the medical device 2 can be made smaller in overall size.

The operating member 41 is configured to be capable of moving the first moving portion 31 and the second moving portion 32 in the same direction along the axial direction with different traveling distances, and movement of the first moving portion 31 and the second moving portion 32 makes the elongate member 10 perform an advance/retraction action and a bending action. Therefore, an actuating member 6 with enhanced performance can be provided.

In addition, because the cam member is comprised of the first cam member 70 and the second cam member 80, which are separate bodies, the first cam member 70 and the second cam member 80 can be made to be different in rotation amount per revolution of the operating member 41 and/or in rotation direction when the operating member 41 is rotated. Consequently, movements of the first moving portion 31 and the second moving portion 32 attendant on rotation of the operating member 41 can be precisely set, and the degree of freedom in setting the bending of the elongate member 10 can be enhanced.

Further, because the second cam member 80 of the first and second cam members 70 and 80 is formed to be integral with the operating member 41, it is unnecessary to provide a transmission mechanism for transmitting a rotating force of the operating member 41 to the second cam member 80, so that the medical device 2 can be made smaller in overall size.

Modification examples of the aforementioned embodiments will be described below by way of example.

FIGS. 7A to 10B are side sectional views of actuating members 5A to 5D of medical devices according to Modification Examples 1 to 4, respectively. Note that in FIGS. 7A to 10B, other configurations than the actuating members 5A to 5D and the sealing portion 65 are omitted.

Modification Example 1

Figure 7A:
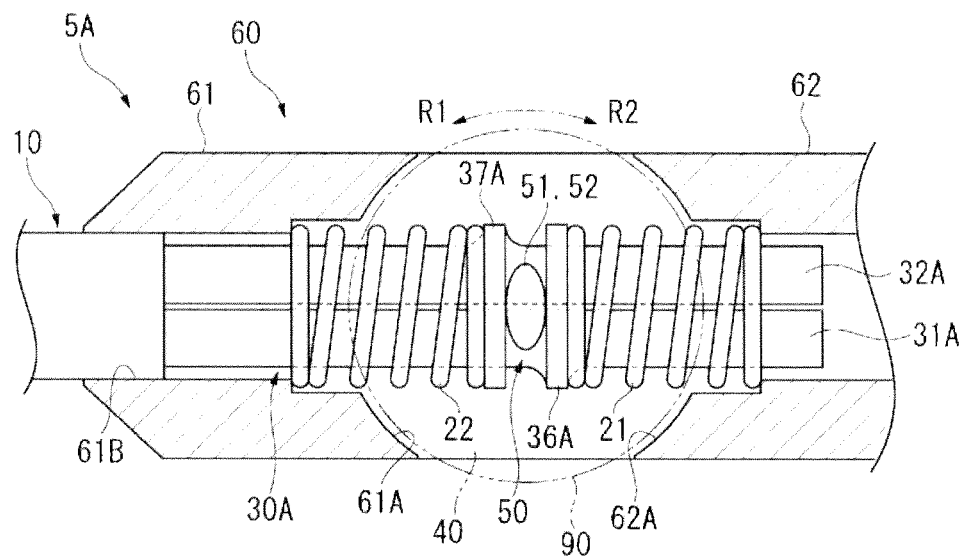
FIGS. 7A and 7B are side sectional views of an actuating member of a medical device according to a Modification Example 1.

The actuating member 5A shown in FIG. 7A includes a push/pull member 30A and a cam member 50. Note that the actuating member 5A is the same as that in the first embodiment otherwise.

In the push/pull member 30A, a first moving portion 31A has an annular first locking portion 36A, which surrounds the first moving portion 31A and a second moving portion 32A in a circumferential direction. The first locking portion 36A is fixed to a peripheral surface of the first moving portion 31A and retains the second moving portion 32A so that the second moving portion 32A can advance/retract. The first locking portion 36A is biased toward a distal side by a first coil spring 21 supported by a gripping portion 62.

The second moving portion 32A has a second locking portion 37A, which surrounds the first moving portion 31A and the second moving portion 32A in the circumferential direction. The second locking portion 37A is fixed to a peripheral surface of the second moving portion 32A and retains the first moving portion 31A so that the first moving portion 31A can advance/retract. The second locking portion 37A is biased toward a proximal side by a second coil spring 22 supported by a supporting portion 61.

The cam member 50 is configured similarly to that in the first embodiment. Here, an outer peripheral surface of the cam member 50 makes contact with both the first locking portion 36A and the second locking portion 37A, and the entire outer peripheral surface constitutes both a first cam surface 51 and a second cam surface 52.

Figure 7B:
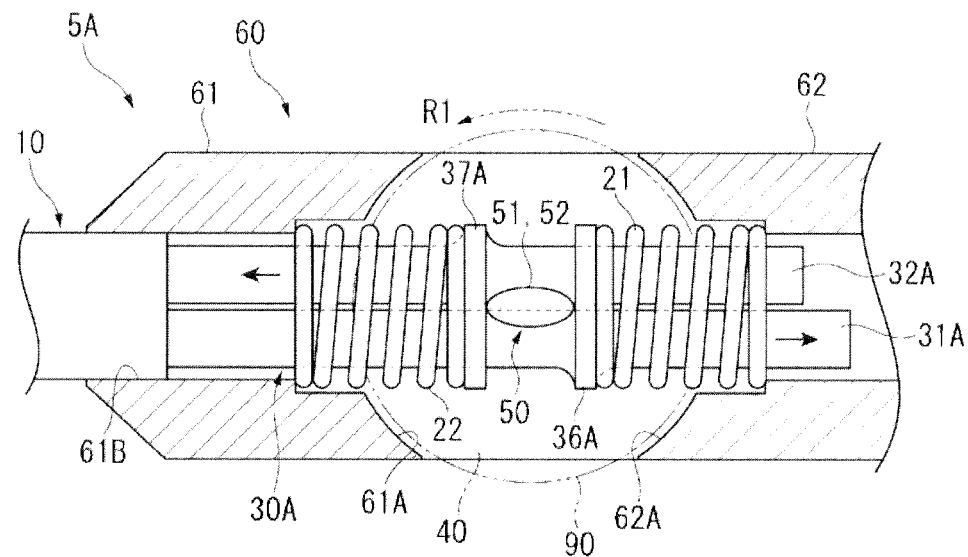

According to this configuration, when the operating member 40 is rotated in a direction R1, as shown in FIG. 7B, the first moving portion 31A is moved toward the proximal side as the first locking portion 36A is guided by the first cam surface 51, whereas the second moving portion 32A is moved toward the distal side as the second locking portion 37A is guided by the second cam surface 52. As a result, bending portions 35 are bent downward, so that the distal side of the elongate member 10 is bent downward.

On the other hand, when the operating member 40 is rotated in a direction R2, the first moving portion 31A is moved toward the proximal side, whereas the second moving portion 32A is moved toward the distal side. Consequently, the bending portions 35 are bent downward, whereby the distal side of the elongate member 10 is bent downward.

Modification Example 2

Figure 8A:
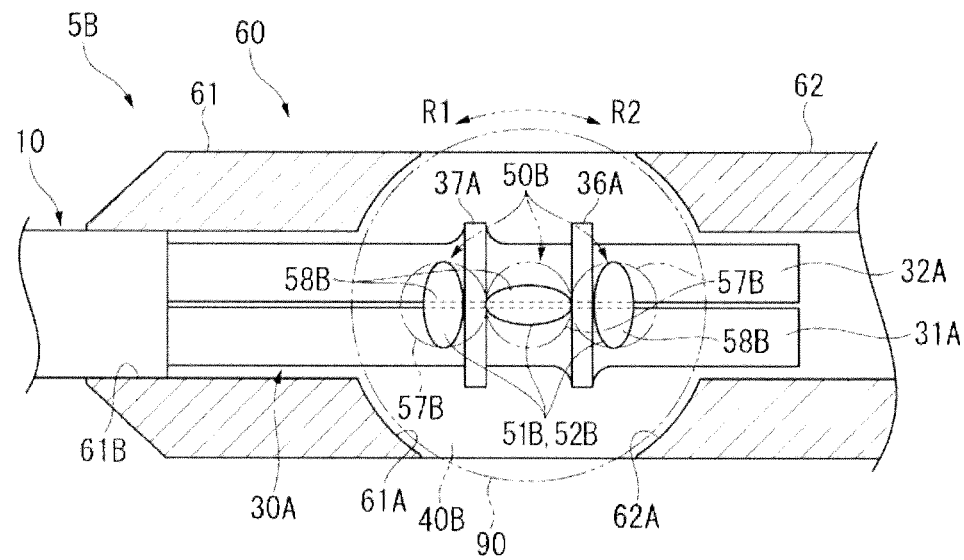
FIGS. 8A and 8B are side sectional views of an actuating member of a medical device according to a Modification Example 2.

The actuating member 5B shown in FIG. 8A differs from the actuating member 5A of Modification Example 1 in that a cam member 50B is provided in place of the cam member 50 and two additional cam members 50B are provided in place of the first coil spring 21 and the second coil spring 22.

The cam members 50B each include a gear portion 57B formed with teeth at a peripheral surface thereof, and a cam portion 58B provided at a surface on one side of the gear portion 57B. The three cam members 50B are juxtaposed in the axial direction of an elongate member 10 with their gear portions 57B in mesh, and the central cam member 50B is formed to be integral with an operating member 40B.

The cam portion 58B extends from a rotation center of the gear portion 57B toward one side and the other side along a radial direction of the gear portion 57B. An outer peripheral surface of the cam portion 58B makes contact with both a first locking portion 36A and a second locking portion 37A, and the entire outer peripheral surface constitutes both a first cam surface 51B and a second cam surface 52B.

Figure 8B:
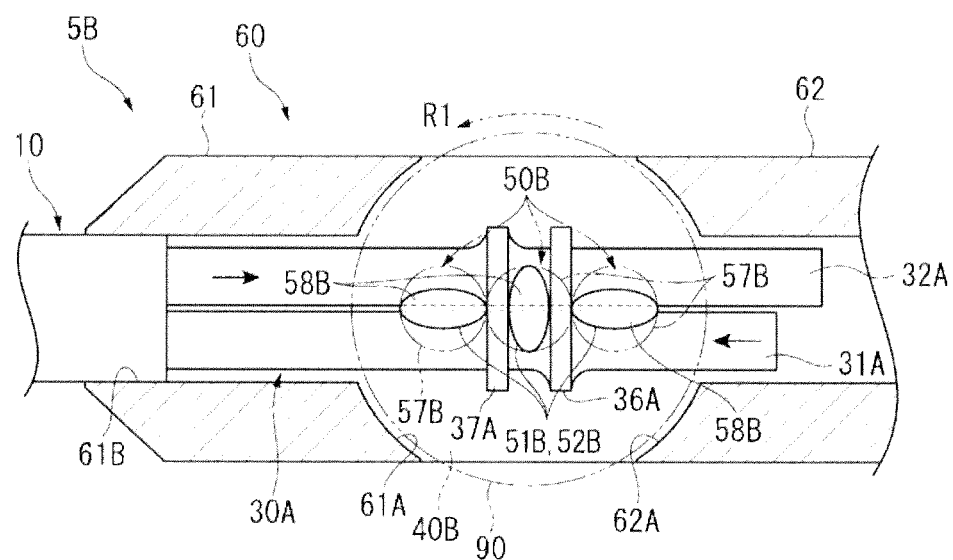

According to this configuration, as shown in FIG. 8B, when the operating member 40B is rotated, the elongate member 10 is bent in a manner similar to that in the case of Modification Example 1. An operating force for the operating member 40B can be reduced as compared to that in Modification Example 1 because a first moving portion 31A and a second moving portion 32A are not biased.

Modification Example 3

Figure 9A:
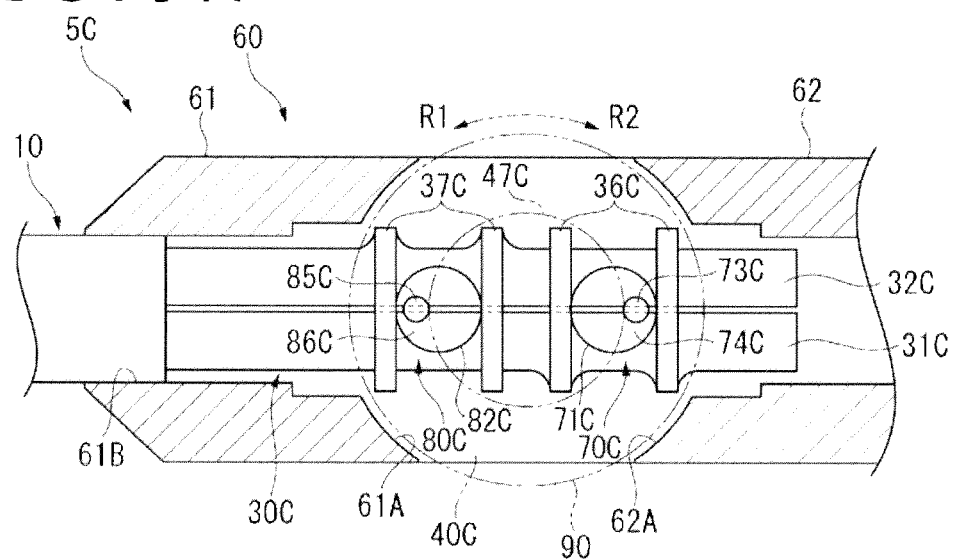
FIGS. 9A and 9B are side sectional views of an actuating member of a medical device according to a Modification Example 3.

The actuating member 5C shown in FIG. 9A includes a push/pull member 30C, an operating member 40C, a first cam member 70C, and a second cam member 80C.

In the push/pull member 30C, a first moving portion 31C has two annular first locking portions 36C, which surround the first moving portion 31C and a second moving portion 32C in a circumferential direction. The first locking portions 36C are fixed to a peripheral surface of the first moving portion 31C, and retain the second moving portion 32C so that the second moving portion 32C can advance/retract.

The second moving portion 32C has two annular second locking portions 37C, which surround the first moving portion 31C and the second moving portion 32C in the circumferential direction. The second locking portions 37C are fixed to a peripheral surface of the second moving portion 32C, and retain the first moving portion 31C so that the first moving portion 31C can advance/retract.

The operating member 40C is composed of a disk-shaped member having a disk surface formed with a gear portion 47C, and is configured to effect movement of the first moving portion 31C and the second moving portion 32C by rotation of the operating member 40C.

The first cam member 70C includes a first gear portion 73C meshing with the gear portion 47C, and a first cam portion 74C provided at a surface on one side of the first gear portion 73C. The first gear portion 73C is provided at an eccentric position relative to the center of the first cam portion 74C. The first cam portion 74C is formed in a circular shape and provided between the two first locking portions 36C, making contact with each of the first locking portions 36C. An outer peripheral surface of the first cam portion 74C constitutes a first cam surface 71C.

The second cam member 80C includes a second gear portion 85C meshing with the gear portion 47C, and a second cam portion 86C provided at a surface on one side of the second gear portion 85C. The second gear portion 85C is provided at an eccentric position relative to the center of the second cam portion 86C. The second cam portion 86C is formed in a circular shape and provided between the two second locking portions 37C, making contact with each of the second locking portions 37C. An outer peripheral surface of the second cam portion 86C constitutes a second cam surface 82C.

Figure 9B:
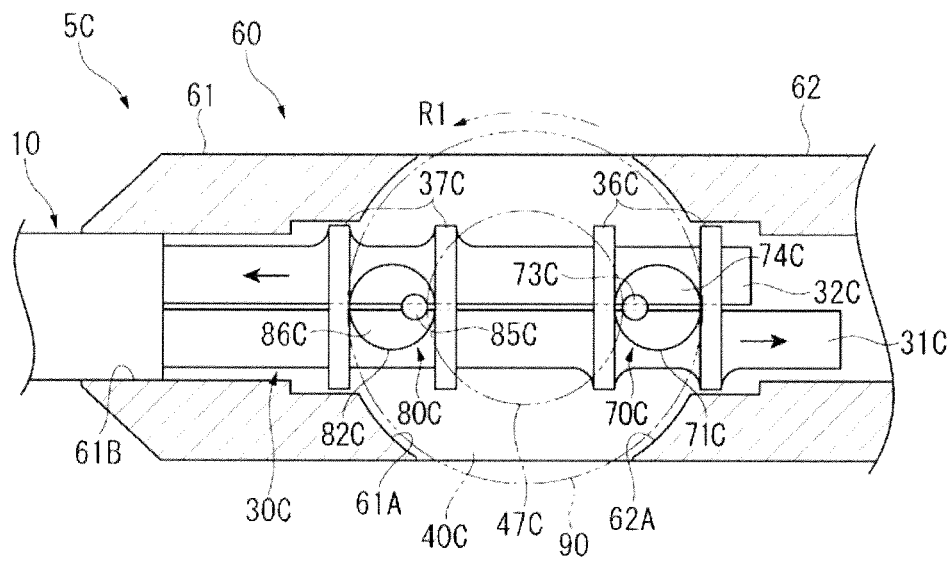

According to this configuration, when the operating member 40C is rotated in either of a direction R1 and a direction R2, as shown in FIG. 9B, the first moving portion 31C is moved toward a proximal side as the first locking portion 36C is guided by the first cam surface 71C, while the second moving portion 32C is moved toward a distal side as the second locking portion 37C is guided by the second cam surface 82C. As a result, bending portions 35 are bent downward, whereby the distal side of an elongate member 10 is bent downward.

Modification Example 4

Figure 10A:
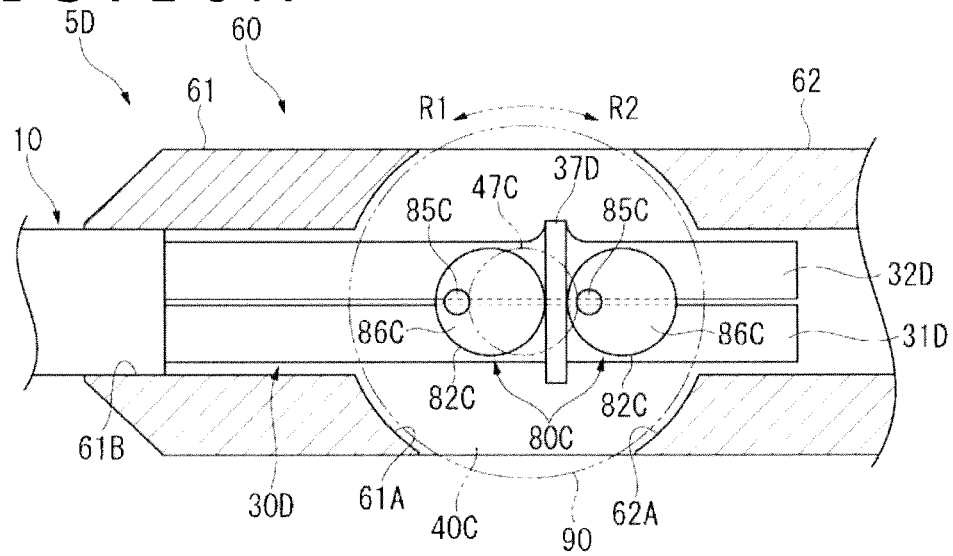
FIGS. 10A and 10B are side sectional views of an actuating member of a medical device according to a Modification Example 4.

The actuating member 5D shown in FIG. 10A includes a push/pull member 30D, an operating member 40C, and second cam members 80C.

In the push/pull member 30D, a second moving portion 32D has an annular second locking portion 37D, which surrounds a first moving portion 31D and the second moving portion 32D in a circumferential direction. The second locking portion 37D is fixed to a peripheral surface of the second moving portion 32D, and retains the first moving portion 31D so that the first moving portion 31D can advance/retract.

The two second cam members 80C are juxtaposed in an axial direction of an elongate member 10, with their gear portions 85C meshing with a gear portion 47C. These second cam members 80C are disposed in such an orientation that their gear portions 85C are in line symmetry with each other, with the gear portion 47C interposed therebetween.

Figure 10B:
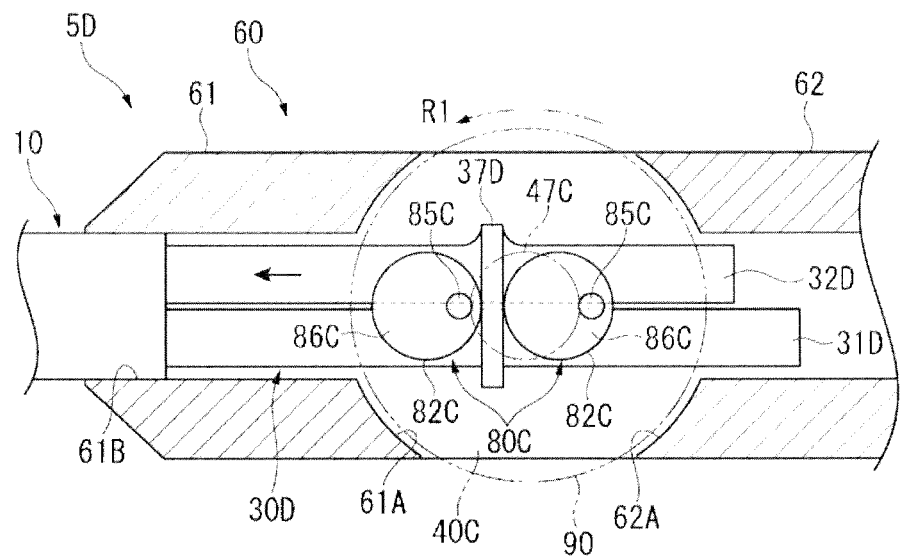

According to this configuration, when the operating member 40C is rotated in either of a direction R1 and a direction R2, as shown in FIG. 10B, the first moving portion 31D is not moved toward a distal side nor toward a proximal side, and only the second moving portion 32D is moved toward the distal side. As a result, bending portions 35 are bent downward, whereby the distal side of an elongate member 10 is bent downward.

Note that the present disclosure is not limited to the aforementioned embodiments and modification examples, and that various changes, improvements and the like could be effected therein by one skilled in the art without departing from the spirit or scope of the disclosure as defined in the appended claims.

For instance, in the first embodiment, the first locking portion 36 may be provided on the proximal side relative to the rotation center RC, and the second locking portion 37 on the distal side relative to the rotation center RC, in a condition where the bending portions 35 are not bent.

In addition, the first locking portion 36 and the second locking portion 37 may be formed in recessed forms in the moving portions 31 and 32 instead of cutting out the moving portions 31 and 32.

In the second embodiment, the first cam member 70 may, in place of the second cam member 80, be formed to be integral with the operating member 41. In addition, the operating member 40C may be adopted in place of the operating member 41, the first cam member 70 and the second cam member 80 may be provided as separate bodies from the operating member 40C, and the first gear portion 73 of the first cam member 70 and the second gear portion 85 of the second cam member 80 may be meshed with the gear portion 47C of the operating member 40C. In these cases, it is sufficient that the positions of the first locking portion 36 and the second locking portion 37 are matched to the positions of the first cam member 70 and the second cam member 80.

Each of the cam members 50, 50B, 70, 70C, 80, and 80C may assume any shape so long as they enable the first moving portion 31, 31A, 31C, or 31D and the second moving portion 32, 32A, 32C, or 32D to be axially moved relative to each other. For example, each of the cam surfaces 51, 51B, 52, 52B, 71, 71C, 82, and 82C may be formed in a non-symmetrical shape so that the traveling amount of each of the moving portions 31, 31A, 31C, 31D, 32, 32A, 32C, and 32D when the operating member 40, 40B, 40C, or 41 is rotated in the direction R1 and the traveling amount of each moving part when the operating member is rotated in the direction R2 are different from each other.

The operating member 40, 40B, 40C, or 41 may adopt configurations other than the aforementioned embodiments and modification embodiments so long as the operating member is rotatable about an axis in a direction intersecting the axial direction of the elongate member 10 at a rotation center RC, and is capable of effecting movement of the first moving portion 31 and the second moving portion 32. For instance, the operating member 40, 40B, 40C, or 41 may be provided with teeth at an outer periphery thereof so as to be a pinion, and a rack may be meshed with the pinion so that the operating member 40, 40B, 40C, or 41 can be rotated by a sliding operation of the rack. Further, the operating member may be formed in the shape of a lever such that the operating member is rotatable, with a longitudinally substantially middle point of the operating member as a rotation center RC.

The push/pull member 30 may not include the connecting portion 39. In this case, for example, when end portions on the distal side with respect to the axial direction of the elongate member 10 of the bending portions 35 are connected to the elongate member 10, the elongate member 10 can be bent.

In addition, the elongate member 10 may have any configuration that permits the elongate member 10 to be bent.

The push/pull member 30, 30A, 30C, or 30D may not have the sealing portion 65. According to this configuration, a treatment device can be inserted and passed from the proximal side of the base portion 60 and through the lumen defined by the push/pull member 30, 30A, 30C, or 30D, so that a part on the distal side beyond the connecting portion 39 of a body lumen or cavity can be treated.

The present disclosure is applicable not only to medical devices for use in diagnosis or treatment of paranasal sinus but also to any other medical devices that have a bendable elongate body.

What is claimed is:

1. An actuating member for making a flexible elongate member for medical use perform a predetermined action, the actuating member comprising:
a push/pull member comprising:
first and second divided portions that together form a tube-shaped structure and that are divided in a circumferential direction of the tube-shaped structure,
wherein the first divided portion includes a first moving portion disposed on a proximal side in an axial direction of the elongate member, and a first extending portion that extends from the first moving portion toward a distal side in the axial direction of the elongate member,
wherein the second divided portion includes a second moving portion disposed on the proximal side in an axial direction of the elongate member, and a second extending portion that extends from the second moving portion toward a distal side in the axial direction of the elongate member,
wherein the first and second moving portions are movable relative to each other in the axial directed of the elongate member,
wherein the push/pull member is configured to be pushed and pulled in the axial direction of the elongate member in conjunction with a movement of the first moving portion and the second moving portion,
wherein the first moving portion includes a first divided surface, and the second moving portion includes a second divided surface, the first and second divided surfaces being surfaces along which the first moving portion is divided from the second moving portion,
wherein the first divided surface of the first moving portion includes a first concave surface, and
wherein the second divided surface of the second moving portion includes a second concave surface;
an operating member configured to effect the movement of the first moving portion and the second moving portion, the operating member being rotatable about an axis in a direction intersecting the axial direction of the elongate member; and
at least one cam member comprising a first cam surface that directly contacts the first concave surface, and a second cam surface that directly contacts the second concave surface, such that the at least one cam member is configured to move the first moving portion and the second moving portion in conjunction with rotation of the operating member,
wherein the push/pull member is configured to make the elongate member perform at least one of (i) an advance/retraction action and (ii) a bending action, by transmitting the movement of the first moving portion and the second moving portion, which are moved by the at least one cam member, to the elongate member.

2. The actuating member according to claim 1, wherein the at least one cam member is configured to move the first moving portion and the second moving portion in opposite axial directions, and the movement of the first moving portion and the second moving portion makes the elongate member perform the bending action.

3. The actuating member according to claim 1, wherein the at least one cam member is configured to move the first moving portion and the second moving portion in the same direction along the axial direction with different traveling distances, and the movement of the first moving portion and the second moving portion makes the elongate member perform both (i) the advance/retraction action and (ii) the bending action.

4. The actuating member according to claim 1, wherein the at least one cam member comprises a single member having the first cam surface that contacts the first moving portion and the second cam surface that contacts the second moving portion.

5. The actuating member according to claim 1, wherein the at least one cam member is integrally formed with the operating member.

6. The actuating member according to claim 1, wherein the at least one cam member comprises a first cam member and a second, separate cam member, the first cam member having the first cam surface that makes contact with the first moving portion, and the second cam member having the second cam surface that makes contact with the second moving portion.

7. The actuating member according to claim 6, wherein one of the first cam member and the second cam member is integrally formed with the operating member.

8. The actuating member according to claim 1, wherein the push/pull member is configured to make the elongate member perform at least the bending action, and
wherein the actuating member further comprising a visual recognition portion that enables at least a bending amount of the elongate member to be confirmed by visual recognition.

9. The actuating member according to claim 8, wherein the visual recognition portion comprises a marker or a scale.

10. The actuating member according to claim 1, wherein:
a majority of the first concave surface is located on a distal side of a rotation center of the operating member, and
a majority of the second concave surface is located on a proximal side of the rotation center of the operating member.

11. A medical device comprising:
the actuating member according to claim 1; and
a flexible elongate member, wherein the actuating member is configured to make the flexible elongate member perform at least one of the advance/retraction action and the bending action.

* * * * *